United States Patent
Sugegaya et al.

(10) Patent No.: US 12,236,590 B2
(45) Date of Patent: Feb. 25, 2025

(54) IMAGE DISPLAY APPARATUS AND STORAGE MEDIUM

(71) Applicant: Konica Minolta, Inc., Tokyo (JP)

(72) Inventors: Naotoshi Sugegaya, Hino (JP); Kenta Shimamura, Hino (JP); Noritsugu Matsutani, Musashino (JP)

(73) Assignee: Konica Minolta, Inc., Tokyo (JP)

( * ) Notice: Subject to any disclaimer, the term of this patent is extended or adjusted under 35 U.S.C. 154(b) by 324 days.

(21) Appl. No.: 17/700,778

(22) Filed: Mar. 22, 2022

(65) Prior Publication Data
US 2022/0309660 A1  Sep. 29, 2022

(30) Foreign Application Priority Data

Mar. 23, 2021 (JP) ................. 2021-048943

(51) Int. Cl.
*G06T 7/00* (2017.01)
*G06T 3/40* (2006.01)

(52) U.S. Cl.
CPC .............. *G06T 7/0012* (2013.01); *G06T 3/40* (2013.01)

(58) Field of Classification Search
CPC ................................ G06T 7/0012; G06T 3/40
See application file for complete search history.

(56) References Cited

U.S. PATENT DOCUMENTS

| | | | | |
|---|---|---|---|---|
| 10,413,253 | B2* | 9/2019 | Oh | G16H 30/40 |
| 2003/0086596 | A1* | 5/2003 | Hipp | G06T 7/0012 |
| | | | | 382/128 |
| 2011/0075812 | A1* | 3/2011 | Takekoshi | A61B 6/461 |
| | | | | 378/98.8 |
| 2013/0156267 | A1* | 6/2013 | Muraoka | A61B 6/5217 |
| | | | | 382/103 |
| 2016/0247303 | A1* | 8/2016 | Aoyama | G16H 30/20 |
| 2019/0015056 | A1* | 1/2019 | Sato | A61B 6/12 |
| 2020/0178921 | A1* | 6/2020 | Nanjo | A61B 6/54 |

FOREIGN PATENT DOCUMENTS

| | | |
|---|---|---|
| JP | 2017159192 A | 9/2017 |
| JP | 2019118462 A | 7/2019 |
| JP | 2019180883 A | 10/2019 |
| JP | 2020-089612 A | 6/2020 |

OTHER PUBLICATIONS

Office Action issued in related Japanese Patent Application No. 2021-048943, mailed Jul. 30, 2024, with English translation (6 pages).
Notice of Reasons for Refusal issued in corresponding Japanese Patent Application No. 2021-048943, dated Nov. 12, 2024, with translation (12 pages).

* cited by examiner

*Primary Examiner* — Khai M Nguyen

(57) ABSTRACT

An image display apparatus includes: an input-output interface that obtains medical images of a same target region taken through serial radiography along a time axis; and a hardware processor that: executes a time-series replay display of the medical images obtained by the input-output interface, and displays a position reference at a fixed position on a screen, the position reference being superimposed on each of the medical images during the replay display.

14 Claims, 7 Drawing Sheets

IMAGE DISPLAY APPARATUS AND STORAGE MEDIUM

CROSS-REFERENCE TO RELATED APPLICATIONS

The entire disclosure of Japanese Patent Application No. 2021-048943 filed on Mar. 23, 2021 is incorporated herein by reference.

BACKGROUND

Technical Field

The present invention relates to an image display apparatus and a storage medium.

Description of Related Art

There have been attempts to utilize, for diagnosis, dynamic imaging of a region of a body to be diagnosed (hereinafter called a target region) taken with a semiconductor image sensor, such as an FPD (flat panel detector), while radiological (X-ray) still images taken with a film/screen or a photostimulable phosphor plate have been conventionally used.

More specifically, by making use of high responsivity of a semiconductor image sensor in reading/deleting image data, a dynamic image of a target region is taken by continuously emitting pulsed radiation from a radiation source in sync with timing of reading/deleting of image data with the semiconductor image sensor and performing imaging multiple times per second.

For example, if the target region is the lungs or the heart, a dynamic state of the chest is imaged. With the sequence of images taken and displayed in order, a doctor can observe a sequence of chest movements with breathing, pulsation of the heart, and so forth.

There are also proposed various technologies using a dynamic image of the chest to extract feature quantity information useful for diagnosing ventilation volume by breathing. For example, there is known a technology of: taking dynamic images of the chest from the front and from the side; and obtaining change volume of the lungs as ventilation volume of the lungs on the basis of change in the position of the base of the lungs and the thickness of the lungs.

The presence or absence of adhesions in the lung field is determined by reading the motion picture taken by dynamic imaging. This makes it possible to estimate in advance the time required for incision of adhesions in the surgical plan and to estimate the surgical time with high accuracy.

In order to determine the presence or absence of adhesions, it is necessary to actually check the dynamic video of the lung area and identify the areas that are not moving due to adhesions.

For example, in JP 2020-089612, for the purpose of enabling users to quickly check the results of dynamic imaging and improving their diagnostic efficiency, multiple feature points indicating areas that change over time in dynamics are superimposed on a single medical image to generate an image for display and supplement visibility during reading.

However, when reading images, it is necessary to read not only a single display image, but also the dynamic video itself, and at this time, low visibility remains an issue.

In particular, when reading adhesions in the chest, it is necessary to determine where there is less movement due to the location of the lung adhesions.

In this case, since the movement of the ribs and that of the lungs are independent of each other, the movement of the lungs is easily overlooked due to the movement of the ribs.

SUMMARY

One or more embodiments of the present invention improve the visibility when reading a dynamic movie, which is a time-series replay display of multiple medical images taken in dynamic imaging.

An image display apparatus reflecting one aspect of the present invention is an image display apparatus including: an image obtainer (i.e., input-output interface) that obtains multiple medical images of a same target region taken through serial radiography along a time axis; and a hardware processor that is able to perform replay displaying in time series of the multiple medical images obtained by the image obtainer, and display a position reference at a fixed position on a screen so as to be superimposed on each of the multiple medical images during the replay displaying.

A storage medium reflecting one aspect of the present invention is a non-transitory computer-readable storage medium storing an image display program to cause a computer of an image display apparatus to: obtain multiple medical images of a same target region taken through serial radiography along a time axis; and perform replay displaying in time series of the obtained multiple medical images and display a position reference at a fixed position on a screen so as to be superimposed on each of the multiple medical images during the replay displaying.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF EMBODIMENTS

Hereinafter, embodiments of an image display apparatus (image display system) will be described with reference to the drawings.

In the following, an image display apparatus will be described, but the image display apparatus includes image display systems in which each functional part is distributed and installed in a separate device.

Although the embodiments described below have various limitations, the scope of the present invention is not limited to the embodiments or the illustrated examples.

An image display apparatus in one or more embodiments is included in a medical imaging system, and obtains medical images, such as medical images constituting a radiological dynamic image (hereinafter called a dynamic image), and displays the obtained medical images including the medical images constituting the dynamic image and various kinds of information.

First of all, a relationship between the medical imaging system and the image display apparatus in one or more embodiments is described with reference to FIG. 1.

[Configuration of Medical Imaging System]

Figure 1:
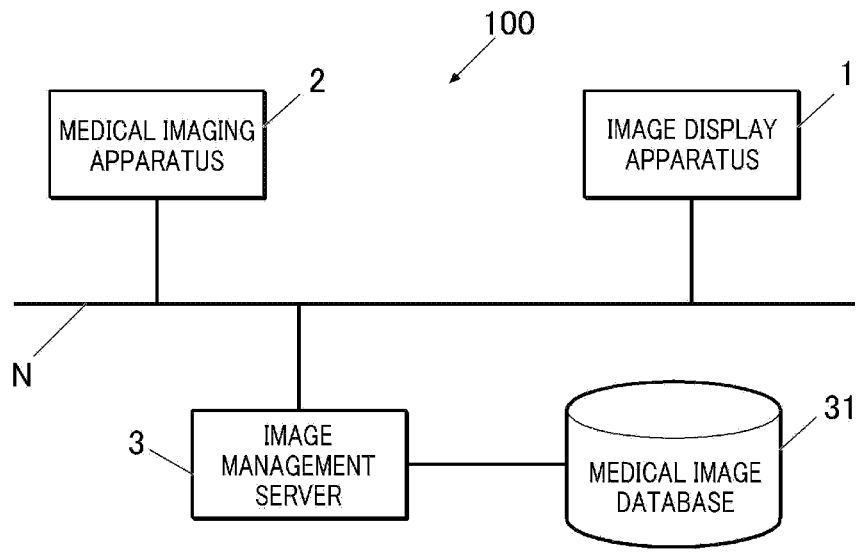
FIG. 1 is a configuration diagram of main components of a medical imaging system including an image display apparatus according to one or more embodiments.

FIG. 1 is an example of configuration of a medical imaging system 100.

The medical imaging system 100 is a system installed in a medical facility, such as a hospital.

As shown in FIG. 1, the medical imaging system 100 includes an image display apparatus 1 (medical image display apparatus), a medical imaging apparatus 2, and an image management server 3. These apparatuses connect to each other for data exchange via a communication network N consisting of a communication line(s), such as a local area network (LAN) and a wide area network (WAN). Each of the components constituting the medical imaging system 100 conforms to digital imaging and communications in medicine (DICOM) standard, and communication between the components is performed in accordance with the DICOM standard.

As to each of the apparatuses constituting the medical imaging system 100, the number of apparatuses is not particularly limited. For example, as the medical imaging apparatus 2, various types of modalities, such as a computed tomography (CT) apparatus, a magnetic resonance imaging (MRI) apparatus, and a computed radiography (CR) apparatus, may be installed. The modalities to be prepared may be the same or different from one another in type. The number of modalities, combinations of the types of modalities, and so forth are determined appropriately to meet the needs of the facility, for example.

The image management server 3 is a computer that accumulates, stores, and manages image data of medical images generated by various modalities (medical imaging apparatus 2) and accessory information on the medical images. Examples of medical images include: tomograms generated by CT apparatuses and MRI apparatuses; and plain roentgenograms generated by CR apparatuses. Medical images in one or more embodiments include medical images constituting a dynamic image that is taken through dynamic imaging by the medical imaging apparatus 2.

Herein, dynamic imaging means imaging of a dynamic state of a target region through serial radiography along a time axis. More specifically, dynamic imaging is performed by: repeatedly emitting pulsed radiation from a radiation source (not illustrated) at predetermined time intervals (pulse emission); or continuously and seamlessly emitting radiation at a low dose rate (continuous emission), thereby continuously imaging the dynamic state of the target region multiple times so as to be a movie. A dynamic image means a sequence of images taken through such imaging and showing a dynamic state of a target region.

The image management server 3 includes a medical image database (DB) 31 that consists mainly of a hard disk. The medical image database 31 stores data of medical images and accessory information on the medical images.

The medical image database 31 stores medical images in the DICOM file format conforming to the DICOM standard. A DICOM file includes an image part and a header part. In the image part, actual data of medical images is written, and in the header part, accessory information on the medical images is written.

The accessory information includes, for example, patient information, examination information, series information, and image detail information.

The patient information includes various kinds of information on a patient of medical images, such as patient identification information for identifying the patient (e.g. patient ID), patient name, sex, and date of birth.

The examination information includes various kinds of information on an examination, such as examination identification information for identifying the examination (e.g. examination ID), the examination date, and a doctor in charge.

The image detail information includes various kinds of information on medical images, such as the time when the images were generated, the name of a file path indicating the location where the medical images are stored, comments on the examination, the location where a lesion is found, and the found result.

The series information includes various kinds of information on a series of medical images, such as: a series number for identifying the series in an examination; type of modality (medical imaging apparatus 2) that generated the medical images of the series; examined region; and, if the medical images constitute a dynamic image, the total number of the frame images in the series and frame numbers, which are given to the respective frame images in the series.

The image management server 3 reads out, in response to a request for medical images sent by the image display apparatus 1 via the communication network N, medical image data from the medical image database 31 and sends the read data to the image display apparatus 1.

[Image Display Apparatus (Image Display System)]

Configuration of the image display apparatus 1 (or the image display system; the same applies to the following) in one or more embodiments is described.

Figure 2:
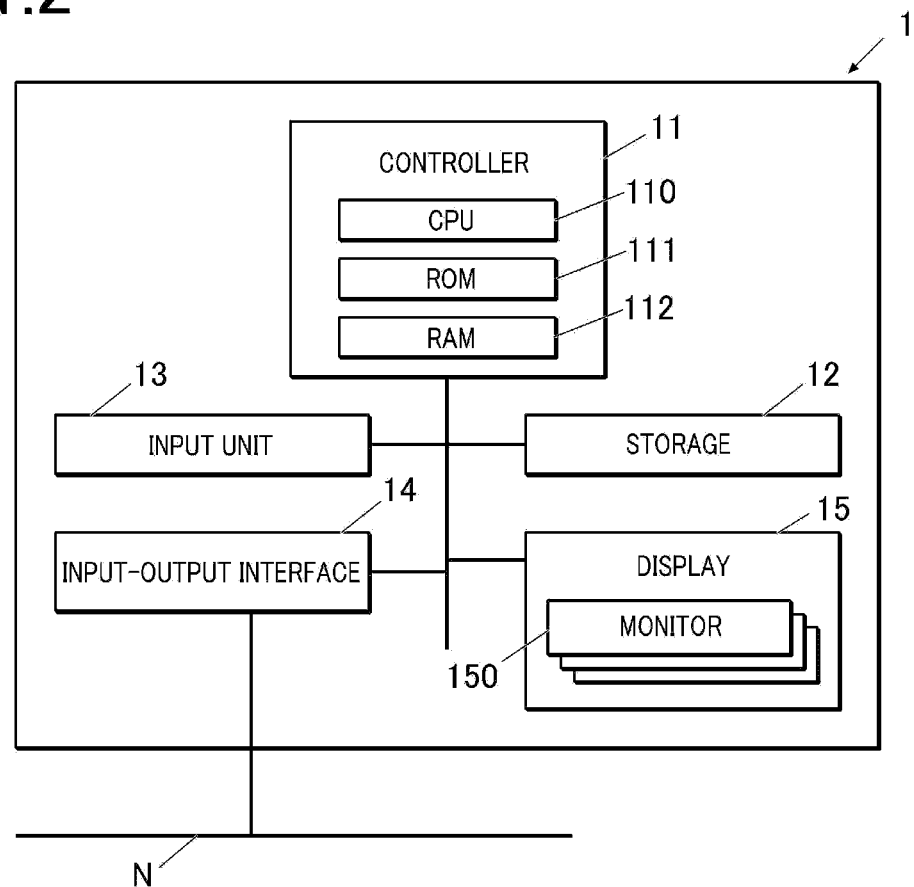
FIG. 2 is a block diagram of main components of the image display apparatus according to one or more embodiments.

FIG. 2 is a block diagram showing configuration of the image display apparatus 1 according to one or more embodiments.

In one or more embodiments, the image display apparatus 1 is a computer that includes a controller 11 (hardware processor), a storage 12, an input unit 13, an input-output interface 14, and a display 15 that connect to a bus as shown in FIG. 2.

The image display apparatus 1 is connected to the communication network N via the input-output interface 14.

In one or more embodiments, the input-output interface 14 is an image obtainer that obtains, via the communication network N, medical images taken through radiography.

The input-output interface 14 as the image obtainer obtains, from the image management server 3 (the medical image database 31 of the image management server 3), a dynamic image of a dynamic state of a target region taken through serial radiography along a time axis.

The image display apparatus 1 may be a general-purpose computer, or can be an apparatus dedicated for medical images.

The image display apparatus 1 may be an integrated apparatus (not illustrated) that includes: a control device, such as a console, controlling an imaging operation of the medical imaging apparatus 2; and an image saving database for saving medical images, such as frame images FI which were taken.

The image display apparatus 1 may be: a desktop personal computer; a notebook computer; a tablet-type terminal device; or a portable terminal device, such as a smartphone.

The controller 11 includes a central processing unit (CPU) 110, a read only memory (ROM) 111, and a random access memory (RAM) 112.

The ROM 111 stores various programs that are performed by the CPU 110, such as a system program and an image display program to function the components for displaying images, and data required for performing these programs. These programs are stored in the ROM 111 in a form of computer readable program code. The CPU 110 operates by following the program code.

The RAM 112 forms, in various kinds of processing performed and controlled by the CPU 110, a work area to temporarily store various programs read out from the ROM 111, input/output data, parameters, and so forth.

The storage 12 includes, for example, a nonvolatile semiconductor memory and/or a hard disk drive (HDD), and stores such as various data.

The storage 12 stores, for example, medical images obtained by the input-output interface 14 as the image obtainer.

The input unit 13 includes, for example, a keyboard, a mouse, and a touchscreen. As described above, the touchscreen is formed over the monitor 150 of the display 15 as one body.

In one or more embodiments, the input unit 13 detects and receives the input operation input by the user touching/tapping the image displayed on the monitor 150. When receiving the input operation, the input unit 13 outputs, to the controller 11, a signal corresponding to the input operation.

In one or more embodiments, the controller 11 controls the display 15 (monitor 150), which is described below, displaying medical images.

The controller 11 of one or more embodiments displays the dynamic image on the display 15 (monitor 150) in a time-series replay display (hereinafter referred to as "dynamic replay displaying").

The controller 11 executes the dynamic replay displaying at a predetermined frame rate.

The controller 11 can display a position reference at a fixed position on the screen so as to be superimposed on each of the multiple medical images that constitute the dynamic image during the dynamic replay displaying.

Figure 3:
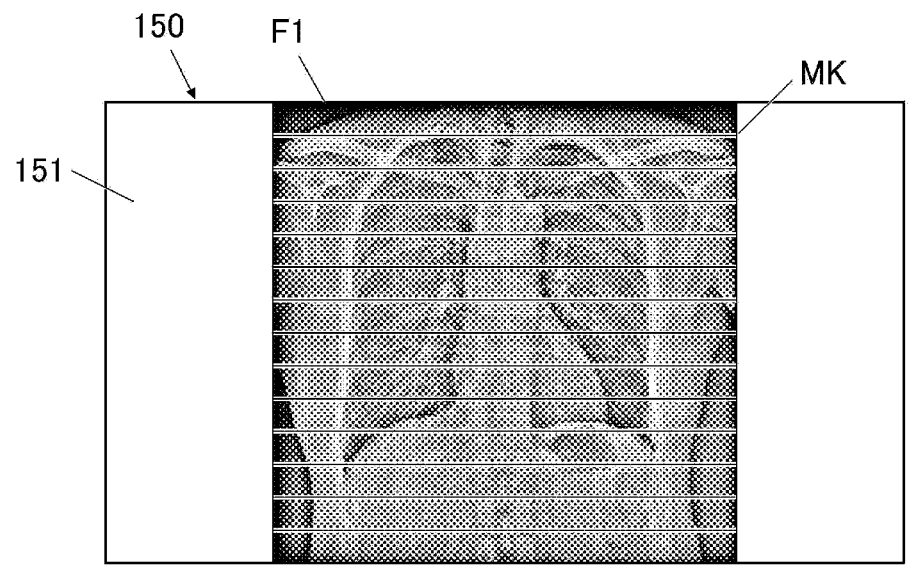
FIG. 3 is a view showing an example of a monitor screen during dynamic replay displaying.
Figure 3:
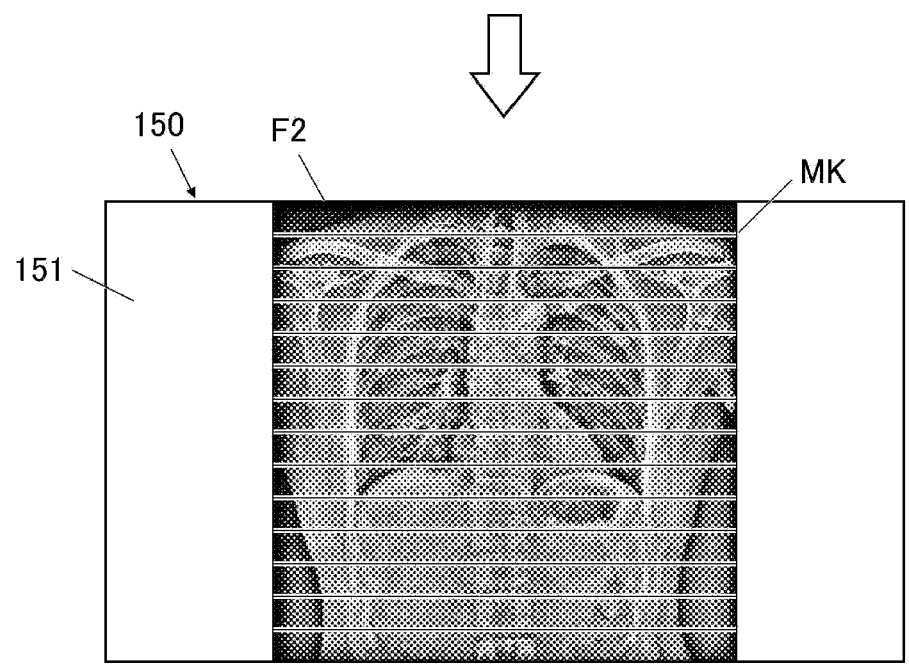

FIG. 3 shows an example of the dynamic replay displaying with position reference MK displayed.

The example shown in FIG. 3 is a dynamic image of the lung field. The frame image F1 shown in FIG. 3 is one of the multiple frame images that make up the dynamic image. The frame image F2 shown in FIG. 3 is one of the multiple frame images that constitute the dynamic image. The frame image F1 and the frame image F2 are images that are separated having the numbers of frames separated in the time series.

For example, it may be understood that frame image F1 is the first frame image and frame image F2 is the dozen-th frame image. The controller 11 starts the dynamic replay displaying based on the operation signal input from the input unit 13 by the user. A frame image F1 is displayed on the monitor 150, and thereafter a frame image F2 is displayed after that, and if there is a frame image beyond that, the dynamic replay displaying continues, and the dynamic replay displaying stops at the last frame image.

As shown in the example in FIG. 3, there is movement in the lung fields during dynamic replay displaying.

On the other hand, the position reference MK is displayed at a fixed position on the screen 151 of the monitor 150 during dynamic replay displaying as described above.

Therefore, by using the position reference MK as a reference (mark), the user can recognize the movement of the lung field (movement of the lungs and ribs) and the magnitude of the movement with high visibility. This will improve the visibility when reading dynamic movies. For example, when reading the adherent part of the lung, it is possible to focus on the movement of the lung instead of the movement of the ribs. This makes it easier to recognize the parts that are moving normally and the parts that are not moving due to abnormalities such as adhesions.

Figure 4:
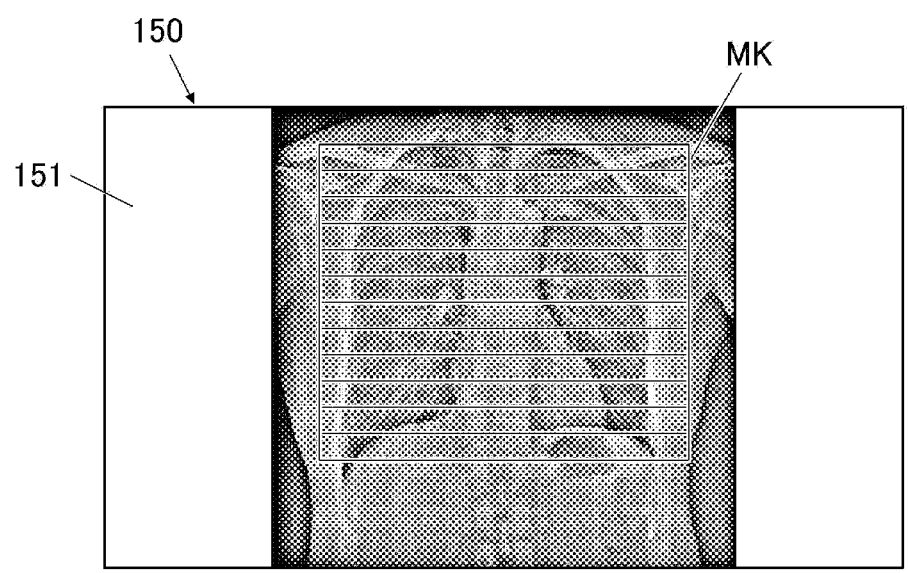
FIG. 4 is a view showing another example of the monitor screen during dynamic replay displaying.

The controller 11 can change the display range of the position reference MK on the screen 151. For example, the controller 11 can make the entire screen 151 the display range of the position reference MK, or make the display range of the dynamic image the display range of the position reference MK as shown in FIG. 3, or make a part of the dynamic image the display range of the position reference MK as shown in FIG. 4.

This allows the user to select the display range of the position reference MK, such as focusing on the part of the image that needs attention, and improves visibility during reading.

The setting for changing the display range of the position reference MK is based on the operation signal input from the input unit 13 by the user.

The controller 11 can also change the position and angle of the position reference MK.

Figure 5:
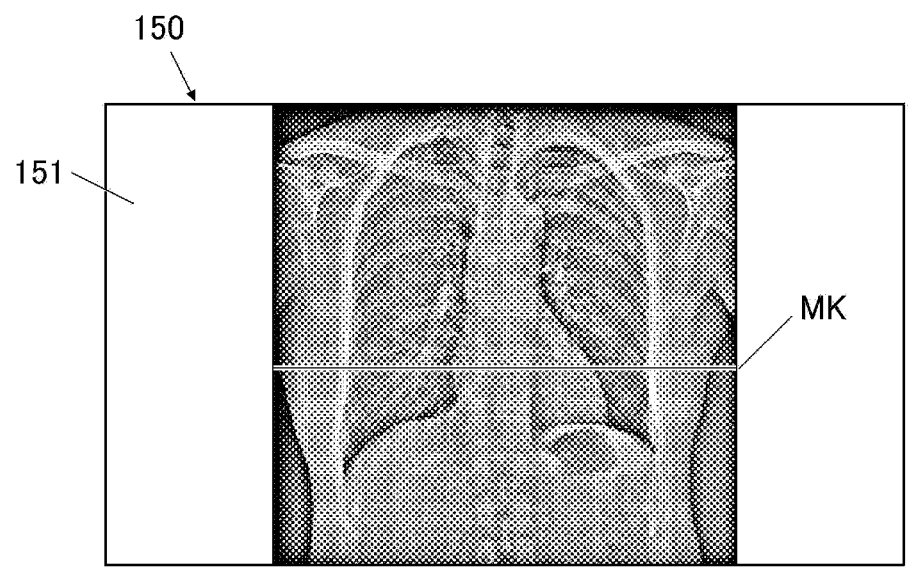
FIG. 5 is a view showing an example of a monitor screen to illustrate how to change the position of a position reference.
Figure 5:
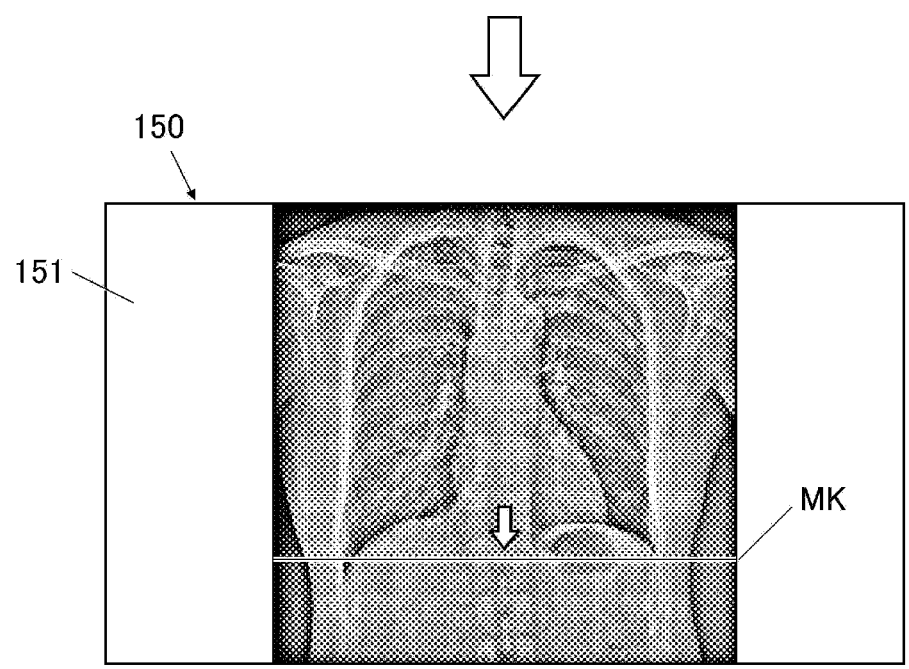

For example, the controller 11 can move the position of the position reference MK up and down as shown in FIG. 5, thus allowing the user to select the position of the position reference MK. In FIG. 5, the position reference MK is shown as a straight line. In the case of equally spaced parallel lines, as in FIG. 3 and FIG. 4, it is possible to change the position of the position reference MK in the same way, which allows the user to select the position of the reference MK and improves visibility during reading.

Figure 6:
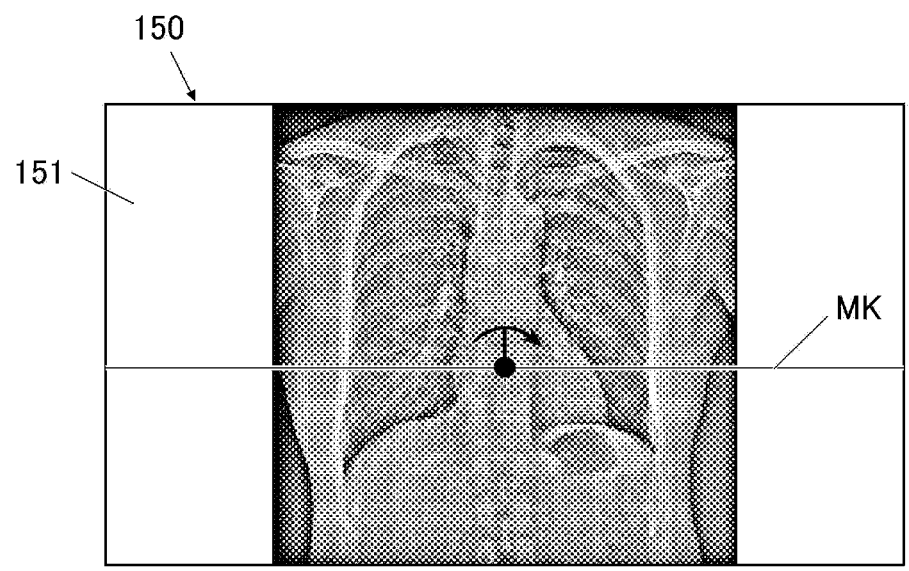
FIG. 6 is a view showing an example of a monitor screen to illustrate how to change the angle of a position reference.
Figure 6:
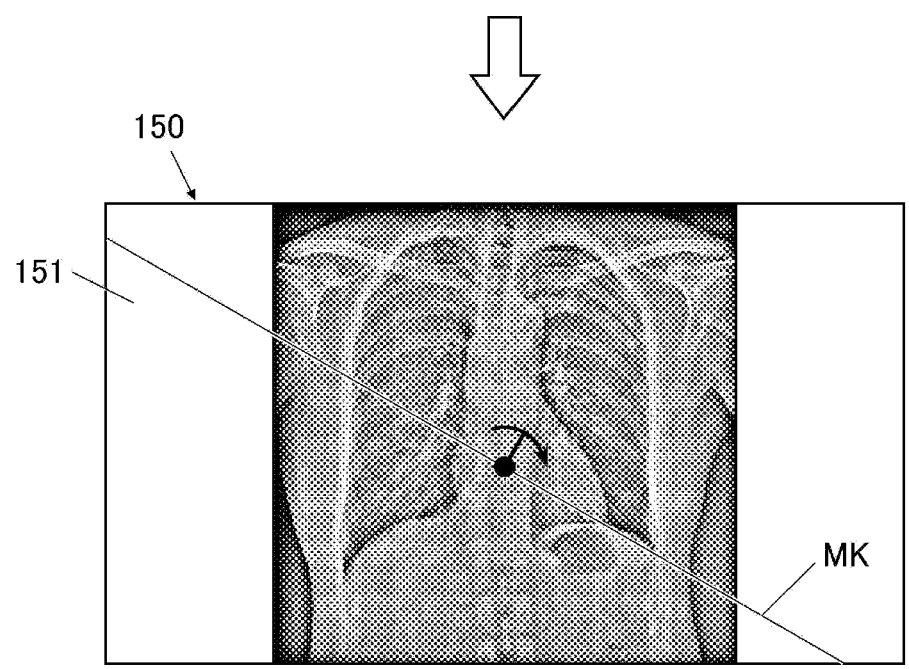

In addition, the controller 11 can change the angle of the position reference MK, as shown in FIG. 6. This allows the user to select the angle of the position reference MK. By placing the position reference MK at a right angle to the direction of movement of the target area to be observed, the movement of the target area can be easily understood. The angle can be set in the range of 360°. The user can choose the angle of the position reference MK, which improves visibility during image reading.

The settings for changing the position and angle of the position reference MK are also based on the operation signals input from the input unit 13 by the user.

In addition, the controller 11 allows the user to select the position and angle at which two parallel straight lines pass through each other, and displays equally spaced parallel lines (three or more) including the two lines as position reference MK. For example, if the user specifies two parallel lines passing through the upper and lower ends of the lung, the angle of the two lines, and the number of parallel lines that fall between the two lines, the controller 11 can display, as the position reference MK, parallel lines of the position, angle, and pitch according to this.

Only one of the position and angle of position reference MK can be changed.

In addition, the controller 11 can select and set one or more of the following: the interval of parallel lines, the number of lines, and the thickness of the lines as shown in FIG. 3 and FIG. 4.

This allows the user to select a configuration of parallel lines that is easy to see, thereby improving visibility during reading. The settings for changing the interval of parallel lines, the number of lines, and the thickness of the lines are also made based on the operation signals input from the input unit 13 by the user.

The controller 11 can also display scaling and panning of medical images during dynamic replay displaying while displaying the position reference MK at a fixed position on the screen 151.

Figure 7:
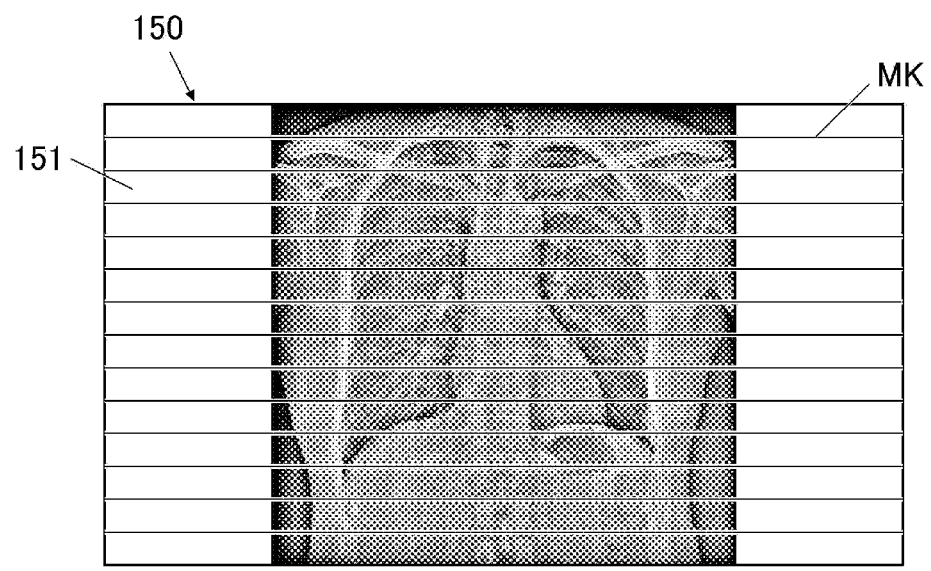
FIG. 7 is a view showing an example of a monitor screen to illustrate how to scale (enlarge/reduce) a medical image.
Figure 7:
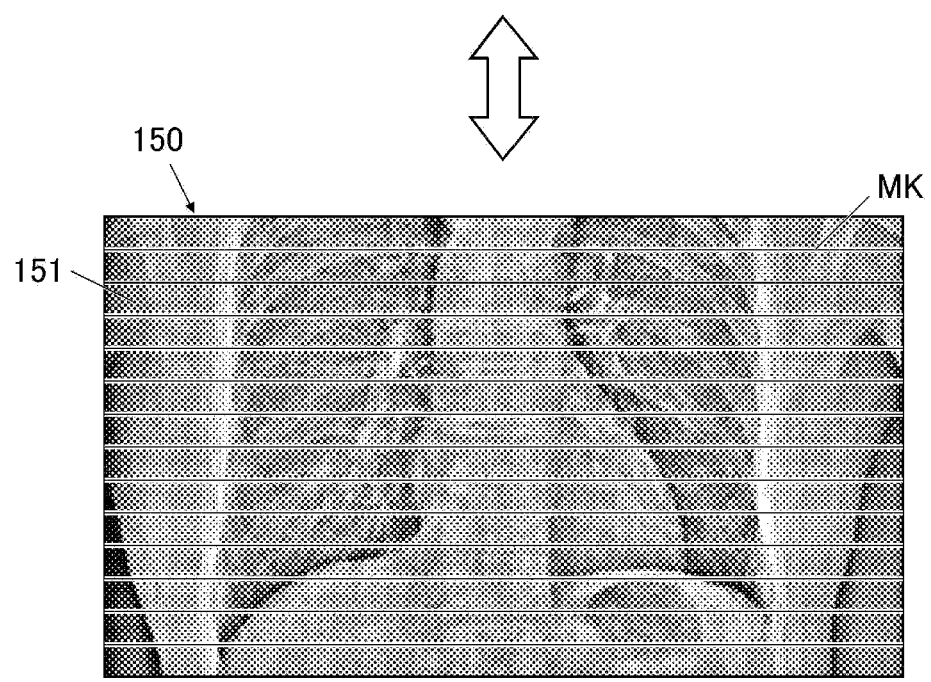
Figure 8:
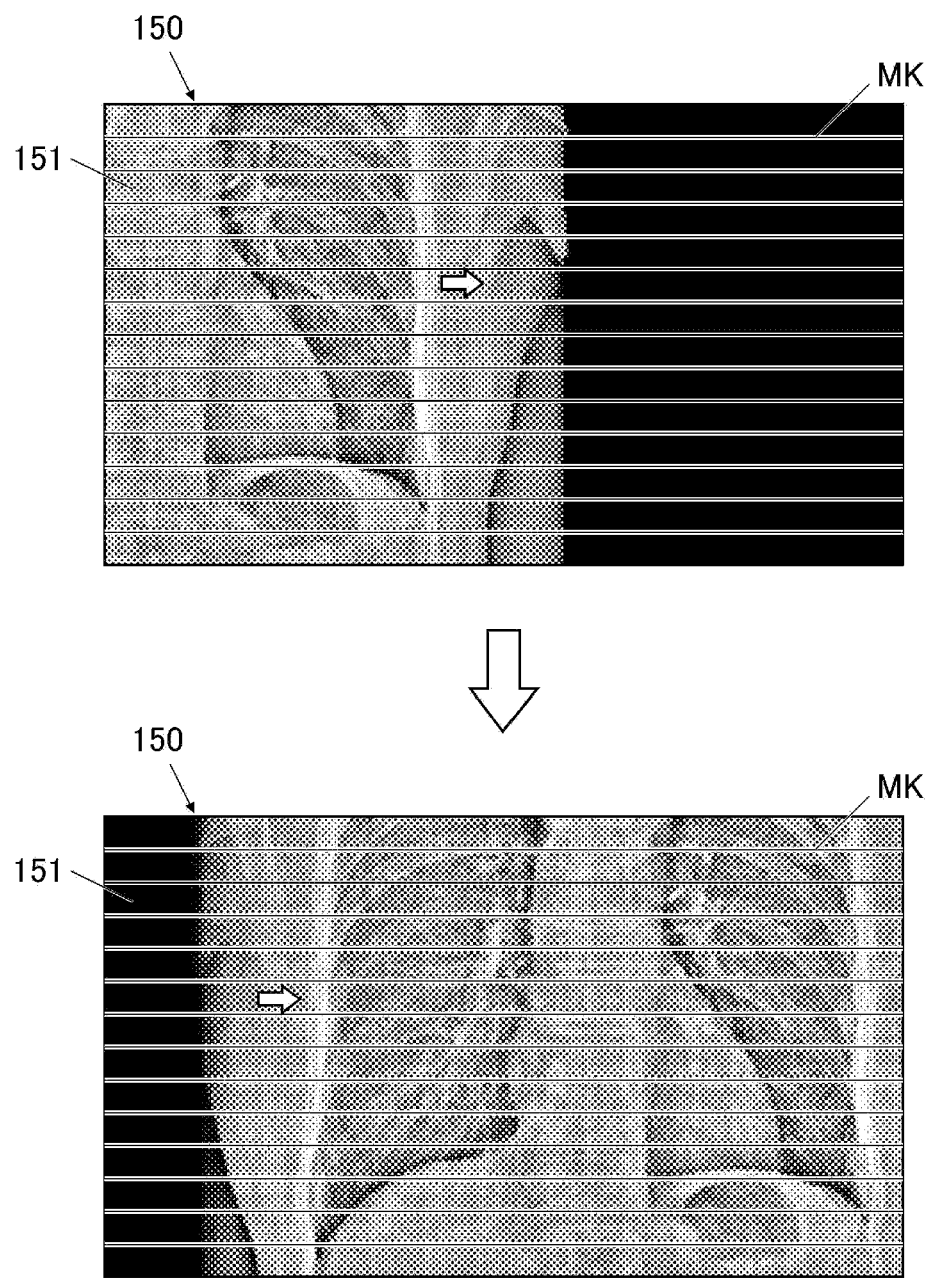
FIG. 8 is a view showing an example of a monitor screen to illustrate how to pan a medical image.

The controller 11 can, for example, display scaling of the medical image as shown in FIG. 7 and panning of the medical image as shown in FIG. 8. The scaling and panning are also performed based on the operation signals input from the input unit 13 by the user. In the case of panning, the position reference MK does not move with respect to the screen 151 even moving is made in a direction that intersects diagonally or vertically with respect to the lines that make up the position reference MK.

In such scaling (FIG. 7) and panning (FIG. 8), the position reference MK is fixed in a fixed position on the screen 151. As the position reference MK does not move, the visibility during image reading is improved.

Only one of scaling and panning can be implemented.

Scaling and panning of medical images may be possible only when the dynamic replay displaying is stopped. In such a case, the dynamic replay displaying is executed if there is a dynamic replay operation, in the display range after the scaling and/or panning that is operated while the display is stopped.

In addition, scaling and panning of medical images may also be performed during dynamic replay displaying. For example, the dynamic replay displaying may be executed by changing the display range according to the pre-defined scaling and/or panning path (key frame setting), or the dynamic replay displaying may be executed by changing the display range according to real-time operations.

In addition, a function to fix the position reference MK to the medical image and to scale and/or pan the position reference MK together with the medical image may also be provided.

The present invention can be used not only for chest examinations, but also for joint examinations and other examinations for the purpose of confirming the working area.

In the above embodiments, there are shown examples of a single straight line and multiple parallel lines as the position reference. However, the form of the position reference is not limited, and it is sufficient as long as it serves as a position reference for the dynamic image. Other forms of position references include grid lines, grid dots, circles, polygons, and other figures.

For the area where the position reference overlaps with the dynamic image, it is possible to set the transmittance of the medical image between 0 and 100%.

According to the above embodiments, it is possible to improve the visibility when reading a dynamic movie which is displayed in time series in a time-series replay displaying of multiple medical images taken in dynamic imaging.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. An image display apparatus comprising:
an input-output interface that obtains medical images of a same target region taken through serial radiography along a time axis; and
a hardware processor that:
executes a time-series replay display of the medical images obtained by the input-output interface,
displays a position reference at a fixed position on a screen, wherein the position reference is superimposed on each of the medical images during the replay display, and
executes at least one of scaling and panning of a medical image among the medical images during the replay display while displaying the position reference at the fixed position without moving the position reference.

2. The image display apparatus according to claim 1, wherein the hardware processor changes a display range of the position reference on the screen.

3. The image display apparatus according to claim 1, wherein the hardware processor changes at least one of a position and an angle of the position reference.

4. The image display apparatus according to claim 1, wherein the hardware processor displays, as the position reference, parallel lines at an equal interval, and executes at least one of scaling and panning of the medical image among the medical images during the replay display while displaying the parallel lines at the fixed position without changing the equal interval of the parallel lines.

5. The image display apparatus according to claim 4, wherein the hardware processor selects and sets at least one of the interval of the parallel lines, a number of the parallel lines, and a thickness of each of the parallel lines.

6. The image display apparatus according to claim 1, wherein the hardware processor executes at least one of scaling and panning of the medical image only when the replay display is stopped.

7. The image display apparatus according to claim 1, wherein the hardware processor changes a display range according to at least one of scaling and panning of the medical image, and executes the replay display in a changed display range.

8. A non-transitory computer-readable storage medium storing an image display program to cause a computer of an image display apparatus to:
obtain medical images of a same target region taken through serial radiography along a time axis;
execute a time-series replay display of the medical images;
display a position reference at a fixed position on a screen, wherein the position reference is superimposed on each of the medical images during the replay display; and
execute at least one of scaling and panning of a medical image among the medical images during the replay display while displaying the position reference at the fixed position without moving the position reference.

9. The storage medium according to claim 8, wherein the image display program causes the computer to change a display range of the position reference on the screen.

10. The storage medium according to claim 9, wherein the image display program causes the computer to change a display range according to at least one of scaling and panning of the medical image; and execute the replay display in a changed display range.

11. The storage medium according to claim 8, wherein the image display program causes the computer to change at least one of a position and an angle of the position reference.

12. The storage medium according to claim 8, wherein the image display program causes the computer to display, as the position reference, parallel lines at an equal interval; and execute at least one of scaling and panning of the medical image among the medical images during the replay display while displaying the parallel lines at the fixed position without changing the equal interval of the parallel lines.

13. The storage medium according to claim 12, wherein the image display program causes the computer to select and set at least one of the interval of the parallel lines, a number of the parallel lines, and a thickness of each of the parallel lines.

14. The storage medium according to claim 8, wherein the image display program causes the computer to execute at least one of scaling and panning of the medical image only when the replay display is stopped.

\* \* \* \* \*